United States Patent
McPhee

[19]

[11] Patent Number: 5,906,597
[45] Date of Patent: May 25, 1999

[54] PATIENT-CONTROLLED DRUG ADMINISTRATION DEVICE

[75] Inventor: Charles J. McPhee, Huntington Beach, Calif.

[73] Assignee: I-Flow Corporation, Irvine, Calif.

[21] Appl. No.: 09/094,111

[22] Filed: Jun. 9, 1998

[51] Int. Cl.⁶ .................................................. A61M 5/00
[52] U.S. Cl. ............................ 604/246; 604/30; 604/48; 604/132; 604/247; 251/5
[58] Field of Search ..................... 604/246, 245, 604/247, 249, 250, 256, 30, 31, 33, 34, 48, 65, 407, 132; 251/5

[56] References Cited

U.S. PATENT DOCUMENTS

| | | | |
|---|---|---|---|
| 2,471,623 | 5/1949 | Hubbell | 251/5 |
| 3,468,308 | 9/1969 | Bierman | 128/214 |
| 3,469,578 | 9/1969 | Bierman | 128/214 |
| 3,831,600 | 8/1974 | Yum et al. | 128/214 R |
| 4,121,584 | 10/1978 | Turner et al. | 128/214 E |
| 4,209,014 | 6/1980 | Sefton | 128/214 F |
| 4,215,689 | 8/1980 | Akiyama et al. | 128/214 F |
| 4,398,908 | 8/1983 | Siposs | 604/31 |
| 4,544,371 | 10/1985 | Dormandy, Jr. et al. | 604/891 |
| 4,548,607 | 10/1985 | Harris | 604/891 |
| 4,559,038 | 12/1985 | Berg et al. | 604/153 |
| 4,588,394 | 5/1986 | Schulte et al. | 604/9 |
| 4,597,758 | 7/1986 | Aalto et al. | 604/256 |
| 4,601,707 | 7/1986 | Albisser et al. | 604/131 |
| 4,626,244 | 12/1986 | Reinicke | 604/141 |
| 4,634,427 | 1/1987 | Hannula et al. | 604/93 |
| 4,668,231 | 5/1987 | de Vries et al. | 604/891 |
| 4,681,560 | 7/1987 | Schulte et al. | 604/9 |
| 4,699,615 | 10/1987 | Fischell et al. | 604/131 |
| 4,828,551 | 5/1989 | Gertler et al. | 604/208 |
| 4,898,584 | 2/1990 | Borsanyi et al. | 604/153 |
| 4,898,585 | 2/1990 | Borsanyi et al. | 604/153 |
| 4,978,338 | 12/1990 | Melsky et al. | 604/93 |
| 5,011,477 | 4/1991 | Winchell et al. | 604/132 |
| 5,061,243 | 10/1991 | Winchell et al. | 604/132 |
| 5,304,153 | 4/1994 | Tsujikawa | 604/132 |
| 5,306,257 | 4/1994 | Zdeb | 604/131 |

*Primary Examiner*—Wynn Wood Coggins
*Assistant Examiner*—N. Kent Gring
*Attorney, Agent, or Firm*—Klein & Szekeres, LLP

[57] ABSTRACT

A PCA device includes a fluid conduit having an upstream portion and a downstream portion, a first flow-restricting orifice in the upstream portion, a second flow-restricting orifice in the downstream portion, a pressure-responsive check valve in the downstream portion in parallel with the second flow-restricting orifice, and a bolus dose delivery mechanism including a chamber in fluid communication between the upstream portion and the downstream portion. Continuous flow is provided through the first flow-restricting orifice, the chamber, and the second flow-restrictive orifice, the continuous flow serving to fill the chamber at a controlled rate through the first flow-restrictive orifice. The bolus dose delivery mechanism is manually actuable to express the contents of the chamber through the check valve to supplement the continuous flow through the downstream portion. The bolus dose delivery mechanism includes a resilient diaphragm that forms a sealed closure for the chamber. The diaphragm is movable from a decompressed position to a compressed position by a plunger that directly engages the diaphragm, and it is restored to the decompressed position by the flow of fluid into the chamber.

20 Claims, 2 Drawing Sheets

PATIENT-CONTROLLED DRUG ADMINISTRATION DEVICE

BACKGROUND OF THE INVENTION

The present invention relates to the field of patient-controlled drug administration devices. More specifically, it relates to an apparatus for administering a medicinal agent to a patient that allows the patient to provide a precisely controlled self-administered bolus dose of the agent in addition to a continuous flow of the agent.

In many clinical situations, it is necessary to administer a continuous flow of a medicinal agent to a patient, and to augment the basal flow periodically or intermittently with a supplemental or "bolus" dose of the agent. This regimen is frequently used in the management of chronic pain, where a continuous flow of an analgesic is maintained by infusion, but a bolus dose of the analgesic is infused at selected times when the patient experiences a sharp increase in the pain. Because most analgesics must be carefully administered to avoid overdosing, the timing and the volume of the bolus doses must be carefully controlled. This control is often exercised by a medical practitioner who administers the bolus dose when it is deemed necessary or desirable.

In chronic care situations, or in home care situations, it is impractical, in many cases, to have a medical practitioner available whenever a patient wants or needs a supplemental bolus dose. Consequently, a number of drug administration devices have been developed that allow the patient to self-administer a controlled bolus dose. These devices (sometimes called patient-controlled administration devices, or "PCA" devices) typically provide a bolus dose that is no more than a predetermined volume, and they also typically include a "lock-out" mechanism, by which is meant a mechanism that limits the frequency of bolus dose administration, or that limits the total bolus dose volume administered over a selected time interval. Some, but not all, prior art PCA devices also allow a controlled continuous flow of the agent between bolus doses. Examples of prior art PCA devices are disclosed in the following U.S. Pat. No. : 4,398,908—Siposs; U.S. Pat. No. 4,544,371—Dormandy, Jr. et al.; U.S. Pat. No. 4,548,607—Harris; U.S. Pat. No. 4,601,707—Albisser et al.; U.S. Pat. No. 4,634,427—Hannula et al.; U.S. Pat. No. 4,668,231—de Vries et al.; U.S. Pat. No. 4,699,615—Fischell et al.; U.S. Pat. No. 4,828,551—Gerler et al.; U.S. Pat. No. 4,898,584—Borsanyi et al.; U.S. Pat. No. 4,898,585—Borsanyi et al.; U.S. Pat. No. 5,011,477—Winchell et al.; U.S. Pat. No. 5,061,243—Winchell et al. and U.S. Pat. No. 5,304,153—Tsujikawa.

Many of the prior art PCA devices are specifically designed to be implantable within the patient's body. For example, of the above-listed patents, the following disclose implantable devices: Dormandy, Jr. et al. '371, Harris '607, Hannula et al. '427, de Vries et al. '231, Fischell et al. '615, Borsanyi et al. '584, and Borsanyi et al. '585. This approach, which requires a surgical procedure for the implantation, may not be suitable for all patients, especially those whose need for the drug is temporary, even if relatively long-term.

Many of the non-implantable PCA devices that have been developed to date are bulky or complex. Such devices are typically expensive to manufacture, and therefore not suitable for single-patient disposable applications. Other devices, while providing convenient delivery of bolus doses on patient demand, require a parallel system for delivery of a continuous flow. An example of the latter type of device is disclosed in U.S. Pat. No. 5,304,153—Tsujikawa.

Thus, there has been a need for a non-implantable PCA device that provides convenient, measured, patient-controlled bolus doses of a therapeutic agent, and that also allows for a regulated continuous or basal flow of the agent. Furthermore, it would be advantageous if such a device were to have a "lock-out" mechanism that limits the total bolus dose volume delivered at any one time or over any specified time interval. In addition, it would be advantageous for such a device to be simply constructed and easily and inexpensively manufactured, so that it may be made as a single-patient disposable apparatus.

SUMMARY OF THE INVENTION

Broadly, the present invention is a PCA device comprising a fluid conduit having an upstream portion and a downstream portion, a first flow-restricting orifice in the upstream portion, a second flow-restricting orifice in the downstream portion, a pressure-responsive check valve in the downstream portion in parallel with the second flow-restricting orifice, and a bolus dose delivery mechanism including a chamber in fluid communication between the upstream portion and the downstream portion. Continuous flow is provided through the first flow-restricting orifice, the chamber, and the second flow-restrictive orifice, the continuous flow serving to fill the chamber at a controlled rate through the first flow-restrictive orifice. The bolus dose delivery mechanism is manually actuable to express the contents of the chamber through the check valve to supplement the continuous flow through the downstream portion.

In a particular preferred embodiment, the bolus dose delivery mechanism comprises a resilient diaphragm that forms a sealed closure for the chamber. The diaphragm is movable from a decompressed position to a compressed position by a plunger that is in direct engagement with the exterior surface of the diaphragm, and it is restored to the decompressed position by the flow of fluid into the chamber.

In operation, a liquid therapeutic agent is continuously delivered, under pressure, to the chamber through the upstream portion at a flow rate controlled by the first flow-restricting orifice. The agent fills the chamber against the resistance offered by the diaphragm, the fluid flow pushing the diaphragm from its compressed to its decompressed position as the chamber fills. A fractional portion of the agent that flows into the chamber also flows out of the chamber, throughout the filling process, through the second flow-restricting orifice. All of the outflow is through the second flow-restricting orifice, the pressure of the flow being less than the cracking pressure of the check valve. When the chamber is filled to capacity, after a predetermined time interval, the diaphragm is in its fully decompressed position, in which it offers little or no resistance to the fluid flow into the chamber. With the chamber filled, the continuous flow rate through the device achieves a predetermined steady state, regulated by the first and second flow-restricting orifices.

When a bolus dose is desired, the plunger is depressed to push the diaphragm toward its compressed position. This compression of the volume of the chamber pressurizes its contents to a pressure above the cracking pressure of the check valve, thereby opening the check valve so that the contents of the chamber are expressed through the check valve. Because the open check valve offers less flow resistance than the second flow-restricting orifice that is in parallel with it, substantially all of the outflow from the chamber is through the check valve, rather than the second flow-restricting orifice.

After the bolus dose is thus delivered, the chamber is refilled, as described above, by the continuous flow of the agent. Because a predetermined time interval must elapse before the chamber is completely refilled and ready to deliver another bolus dose on demand, the maximum volume of the total bolus dose deliverable over any given period of time is defined by a predetermined limit. Thus, the above-described lock-out function is thereby provided.

As will be more fully appreciated from the detailed description that follows, the subject invention provides both a controlled continuous (basal) flow and a controlled bolus dose on demand. The total volume of the bolus dose deliverable over a given period of time is, however, limited to a predetermined maximum by the above-described lock-out function. These capabilities are achieved in device that may be made small enough and light enough in weight to be comfortably worn (e.g., on the wrist) by a patient. Furthermore, a PCA device in accordance with the present invention is simple in construction, and may therefore be manufactured inexpensively, so as to be adapted for single patient, disposable use. Such simplicity also lends itself to reliability and ease of maintenance and care.

DETAILED DESCRIPTION OF A PREFERRED EMBODIMENT

Figure 1:
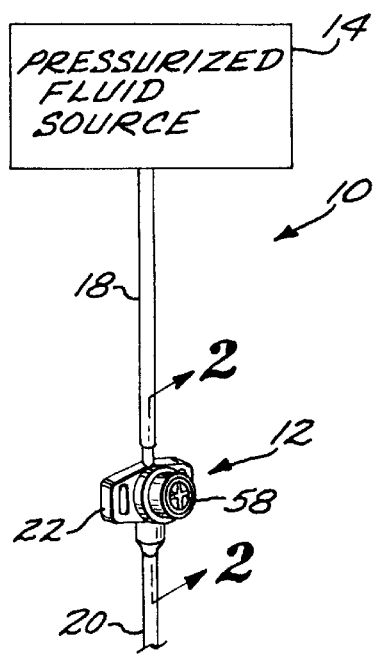
FIG. 1 is a semi-schematic view of a drug infusion system employing a patient-controlled administration (PCA) device in accordance with a preferred embodiment of the present invention.

Referring now to the drawings, FIG. 1 shows a drug infusion system 10 employing a patient-controlled administration (PCA) device 12 in accordance with a preferred embodiment of the present invention. The system comprises a pressurized fluid source 14 that holds a supply of a liquid therapeutic agent, and that pumps the agent into the PCA device 12 through a supply conduit 18 under a predetermined pressure. The supply conduit 18 is fluidly connected to the upstream side of the PCA device 12, as will be described below. The downstream side of the PCA device 12 is fluidly connected to a delivery tube 20, as described below, which terminates in a needle (not shown), which may be configured for intravenous, subcutaneous, intramuscular, or intrathecal injection.

FIGS. 2 through 5 illustrate the PCA device 12 in detail. The device 12 comprises a housing 22 defining a fluid conduit having an upstream portion 24 and a downstream portion 26. The upstream portion 24 is fluidly connectable to the supply conduit 18, while the downstream portion 26 is fluidly connectable to the delivery conduit 20. The fluid conduit of the PCA device 12 includes a chamber 28 having an inlet port 30 in fluid communication with the upstream portion 24 and first and second outlet ports 32, 34 in fluid communication with the downstream portion 26. In a specific preferred embodiment of the invention, the chamber 28 has a maximum volume of about 0.5 ml when filled. A first or upstream flow-restricting orifice 36 is contained within the upstream portion 24, and a second or downstream flow-restricting orifice 38 is contained within the first outlet port 32 at the juncture with the downstream portion 26.

The PCA device 12 includes a bolus dose delivery mechanism, which is best described with reference to FIG. 4. The bolus dose delivery mechanism includes the chamber 28, which is enclosed by the housing 22 on all sides except for one side that is sealed by a resilient diaphragm 40. The diaphragm 40 has a raised central portion 42 that is directly engaged by the inner end of a plunger 44 that is axially movable within a cylindrical fitting 46. The diaphragm 40 also has a peripheral bead 48 that seats in a conforming circular groove 50 in the housing 22. A peripheral skirt 51 is provided circumferentially around the distal (inner) end of the cylindrical fitting 46. The skirt 51 defines an annular slot 52 between itself and the distal end of the fitting 46. The slot 52 receives an annular lip 53 that extends proximally (outwardly) from the housing 22, whereby the fitting 46 is attached to the housing 22 and secured thereto by means such as a suitable adhesive, or by ultrasonic welding. When the fitting 46 is thus attached to the housing 22, the distal (inner) end of the fitting presses the diaphragm bead 48 firmly into the groove 50, creating a fluid-tight seal therebetween.

The plunger 44 has a circumferential ridge 54 that is engageable against the distal or interior-facing side of an annular shoulder 56 within the cylindrical fitting 46. The engagement between the shoulder 56 and the ridge 54 limits the travel of the plunger 44 in the proximal or outward direction within the cylindrical fitting 46 under the resilient force of the diaphragm 40. The plunger 44 is thus captured between the diaphragm 40 and the shoulder 56. The cylindrical fitting 46 has an open proximal or outer end through which the proximal end of the plunger 44 is accessible to the finger or thumb of the patient or other user of the device 12. Thus, the proximal end of the plunger 44 forms a pushbutton 58 (FIG. 1) for manual actuation of the bolus dose delivery mechanism.

Figure 2:
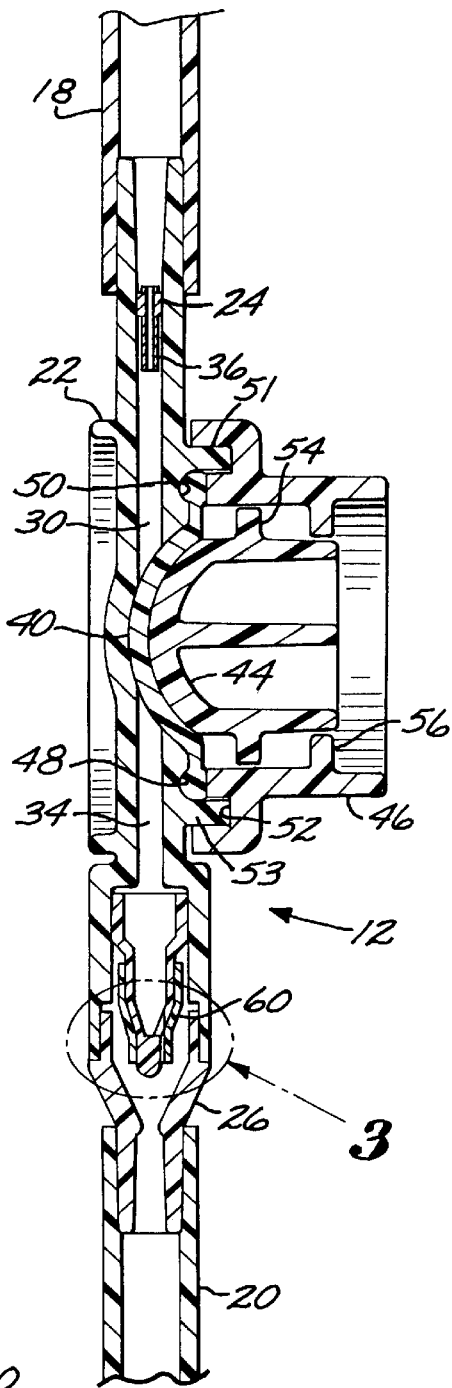
FIG. 2 is a longitudinal cross-sectional view of a PCA device in accordance with a preferred embodiment of the present invention, taken along line 2—2 of FIG. 1, showing the diaphragm of the bolus dose delivery mechanism in its compressed position.
Figure 3:
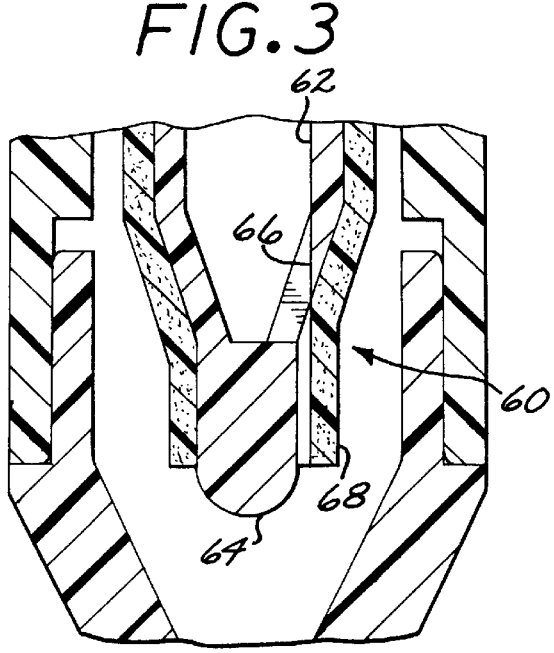
FIG. 3 is an enlarged detailed view of the check valve of the PCA device of FIG. 2, as encompassed within the broken outline 3 of FIG. 2.

Situated within the second outlet port 34 is a check valve 60. As best seen in FIG. 3, the check valve 60 comprises a tubular fitting 62 tapered toward its downstream end, which is terminated by a knob-like valve body 64. An outlet orifice 66 is provided in the tapered portion of the tubular fitting 62 just upstream from the valve body 64. A conformal flexible membrane 68 is fixed around the exterior of the tubular fitting 62, covering the outlet orifice 66 and extending over most of the valve body 64. The membrane 68 functions much as a "duck-bill" valve element, sealing the orifice 66 (as shown in FIGS. 2, 4, and 5) until the fluid pressure in the second outlet port 34 reaches a predetermined "cracking pressure" that separates the membrane 68 from the valve body 64 and thus opens the orifice 66, as shown in FIG. 3.

Figure 4:
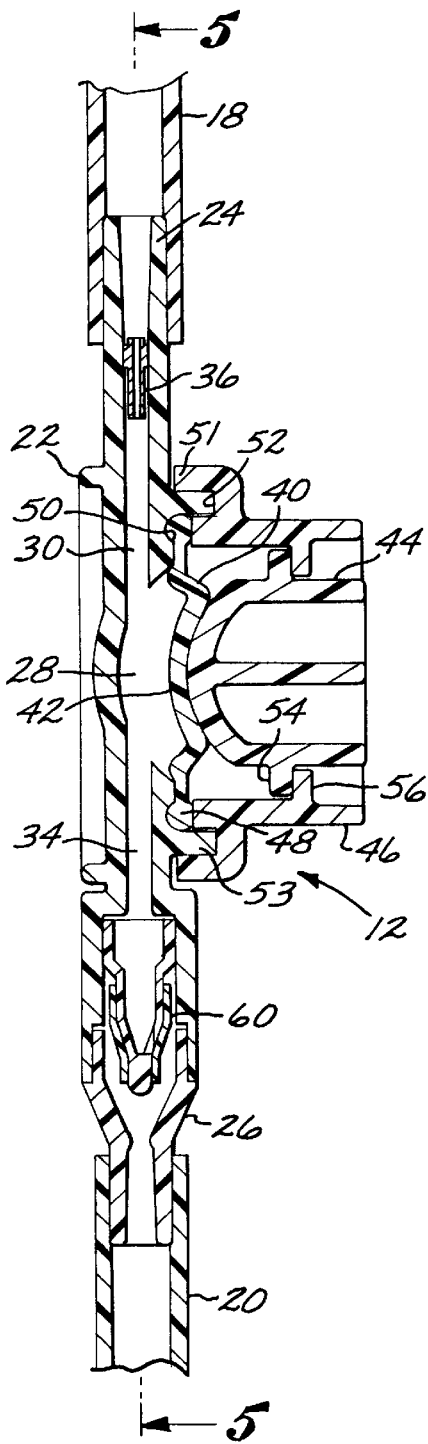
FIG. 4 is a cross-sectional view, similar to FIG. 2, but showing the diaphragm of the bolus dose delivery mechanism in its decompressed position.
Figure 5:
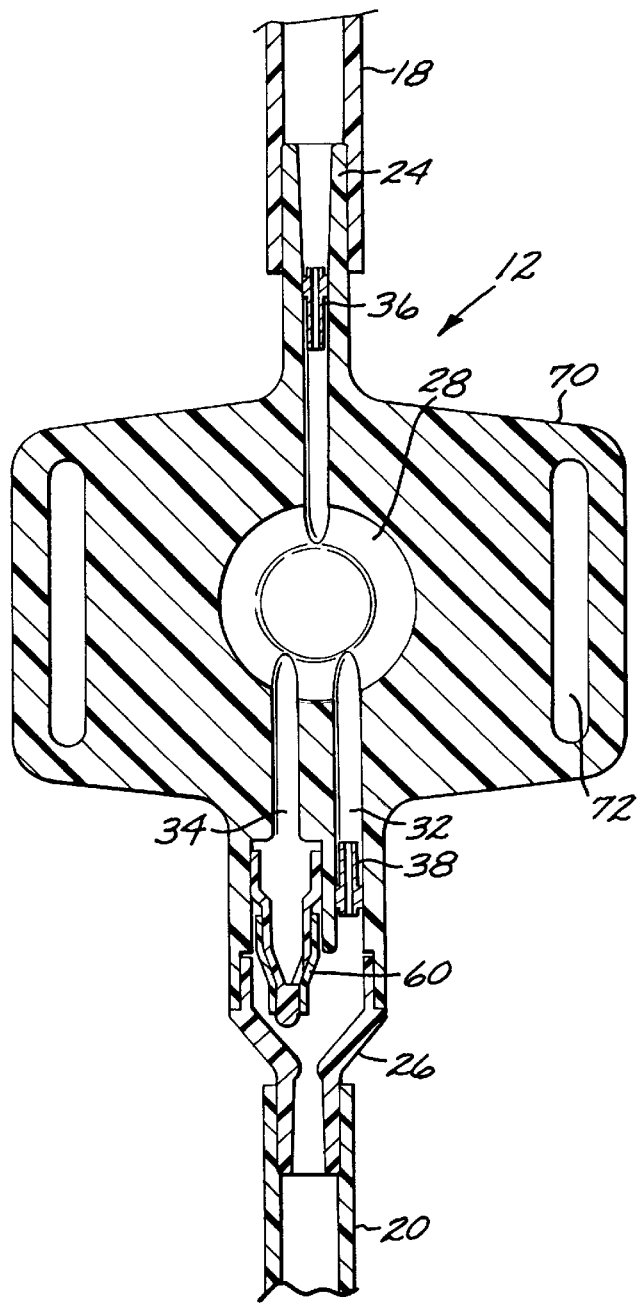
FIG. 5 is a cross-sectional view taken along line 5—5 of FIG. 4.

As best shown in FIG. 4, the housing 22 advantageously is formed with a pair of laterally-extending flaps 70, each of which is provided with a longitudinal slot 72. The slots 72 are configured to accommodate a wrist strap (not shown), allowing the device 12 to be worn on a patient's wrist (not shown).

In operation, a liquid therapeutic agent is continuously delivered from the pressurized fluid source 14 to the chamber 28, through the supply conduit 18, to the upstream portion 24 of the PCA device 12. The liquid flows into the chamber 28 through the inlet 30 at a flow rate that is regulated by the first flow-restricting orifice 36. In a specific preferred embodiment of the invention, the flow rate through the inlet 30 is regulated to about 2.5 ml/hr. The liquid fills the chamber 28, non-linearly versus time, against the diminishing resistance offered by the diaphragm 40, the fluid flow pushing the diaphragm 40 from its compressed position (FIG. 2) to its decompressed position (FIG. 4) as the chamber 28 fills. As the diaphragm 40 is moved from its compressed position to its decompressed position, it pushes the plunger 44 outwardly (in a proximal direction) within the cylindrical fitting 46. The diaphragm 40 reaches its fully decompressed position when the chamber 28 is filled to capacity; at this point, the plunger 44 is pushed to its proximal limit of travel at which its ridge 54 abuts against the shoulder 56.

Throughout the chamber filling process, a fractional portion of the liquid that flows into the chamber 28 also flows out of the chamber 28 through the first outlet port 32, the second flow-restricting orifice 38, and the outlet portion 26. All of the outflow is through the first outlet port 32 and the second flow-restricting orifice 38, because the pressure of the flow is less than the cracking pressure of the check valve 60. This outflow is regulated by the second flow-restricting orifice 38 to about 0.5 ml/hr during the chamber filling process. Thus, with a net inflow into the chamber 28 of about 2.0 ml/hr, the 0.5 ml chamber is filled to capacity in about 15 minutes. As mentioned above, when the chamber 28 is filled to capacity, the diaphragm 40 is at its fully decompressed position. In this position, it offers little or no resistance to the fluid flow through the chamber 28. Consequently, once the chamber 28 is filled, the continuous flow rate through the device increases to a steady state value of about 1.0 ml/hr, limited by the second flow-restricting orifice 38.

When a bolus dose is desired, the plunger 44 is pushed distally into the cylindrical fitting 46 to push the diaphragm 40 toward its compressed position. This results in a compression of the volume of the chamber 28 that pressurizes its contents to a pressure above the cracking pressure of the check valve 60, thereby opening the check valve 60 so that the contents of the chamber 28 are expressed through the check valve orifice 66. Because the open check valve 60 offers less flow resistance that the second flow-restricting orifice 38 that is in parallel with it, substantially all of the outflow from the chamber 28 is through the second outlet port 34 and the check valve 60, rather than the second flow-restricting orifice 38. The outflow from the check valve 60 enters the downstream portion 26 of the fluid conduit defined by the hosing 22, and then enters the delivery tube 20 as a bolus dose of the agent.

After the bolus dose is thus delivered, the chamber 28 is refilled, as described above, by the continuous flow of the liquid agent. As described above, the filling of the chamber 28 returns the plunger 44 to its starling (proximal) position. Thus, no separate spring is required for the plunger's return movement, because the plunger return function is provided by the net effect of the pressurized fluid flow and the resistance of the diaphragm 40. The continuous flow through the first outlet port 32 is re-established almost immediately after the bolus dose is delivered. Because a predetermined time interval (e.g., approximately 15 minutes in a specific preferred embodiment) must elapse before the chamber 28 is completely refilled and ready to deliver another bolus dose on demand, the maximum volume of the total bolus dose deliverable over any given period of time is defined by a predetermined limit. For example, in the specific preferred embodiment described above, the maximum hourly bolus dose volume is 2.0 ml. Thus, the above-described lock-out function is thereby provided to minimize the probability of over-dosing.

It will be appreciated from the foregoing description that the PCA device 12 of the present invention provides both a continuous flow and a bolus dose through nearly identical flow paths, the only difference being that the continuous flow enters the downstream portion 26 through the first outlet port 32, while the bolus dose enters the downstream portion 26 through the second outlet port 34. Thus, parallel delivery systems for the continuous flow and the bolus dose are not required.

Furthermore, as compared with prior art systems employing separate, parallel flow paths for the bolus flow and the continuous flow (e.g., U.S. Pat. No. 5,304,153, supra), the present invention offers significant operational advantages that reduce the likelihood of accidental overdosing. Specifically, if the check valve 60 and/or the downstream flow restricting orifice 38 fails, total fluid flow through the device 12 is limited by the upstream flow restricting orifice 36. If the upstream flow restricting orifice 36 fails, continuous fluid flow to the delivery tube 20 (and thus to the patient) is limited by the downstream flow restricting orifice 38.

All of the components of the PCA device 12, except the diaphragm 40 and the check valve membrane 68, may be made of suitable injection-molded polymeric plastics, as is conventional in the art. The diaphragm 40 and the check valve membrane 68 may be made from any suitable elastomeric polymeric plastic material, as is well-known in the art. Thus, the device 12 may be made inexpensively and therefore acceptable for single-patient, disposable use.

While a preferred embodiment of the invention has been described herein, it will be appreciated that a number of modifications and variations may suggest themselves to those skilled in the pertinent arts. For example, the structure of the check valve 60 described above is exemplary only; other equivalent check valve structures will readily suggest themselves. Also, the structure of the diaphragm 40 may be modified without departing from the scope of the invention. The fluid capacities and flow rates set forth above are likewise exemplary. Furthermore, the specific housing configuration described above may be substantially varied to suit a number of different clinical needs and patient preferences. These and other variations and modifications that may suggest themselves are considered to be within the spirit and scope of the invention, as defined in the claims that follow.

What is claimed is:

1. A device for the administration of a liquid therapeutic agent to a patient, comprising:

a housing defining a fluid flow conduit having an upstream portion and a downstream portion;

chamber in the housing having an inlet lumen in fluid communication with the upstream portion, and first and second outlet lumens separately in communication with the downstream portion;

a check valve in fluid communication with the second outlet lumen that is responsive to a predetermined cracking pressure to allow fluid flow from the second outlet lumen to the downstream portion; and a resilient diaphragm disposed as a sealing closure for the chamber and movable between a compressed position when the chamber is voided of the agent and a decompressed position when the chamber is filled with the agent;

whereby the diaphragm is moved from the compressed position to the decompressed position by the force of the agent filling the chamber from the inlet lumen, during which filling some of the agent flows out of the chamber through the first outlet lumen; and whereby the cracking pressure is created in the second outlet lumen in response to the movement of the diaphragm from the decompressed position to the compressed position, thereby allowing the agent to flow out of the chamber through the second outlet lumen.

2. The device of claim 1, wherein the agent flows from the inlet lumen through the chamber and through the first outlet lumen when the diaphragm is in the decompressed position, and the agent flows from the chamber through the second outlet lumen and the check valve only in response to the creation of the cracking pressure in the second outlet lumen.

3. The device of claim 1, further comprising:
   a first flow-restricting orifice in the upstream portion; and
   a second flow-restricting orifice in the first outlet lumen.

4. The device of claims 1, 2, or 3, wherein the check valve comprises:
   a tubular element having an upstream end in fluid communication with the second outlet lumen and a downstream end in fluid communication with the downstream portion through a valve orifice; and
   a flexible membrane secured to the tubular element so as to cover the valve orifice when the pressure in the second outlet lumen is less than the cracking pressure, whereby the membrane uncovers the valve orifice in response to the pressure in the second outlet lumen being at least equal to the cracking pressure.

5. The device of claims 1, 2, or 3, further comprising a plunger that is engageable against the diaphragm and that is manually movable from a first position to a second position to compress the diaphragm to express the agent from the chamber, and that is returned from the second position to the first position when the diaphragm is moved to the decompressed position as the chamber is filled with the agent.

6. The device of claim 4, further comprising a plunger that is engageable against the diaphragm and that is manually movable from a first position to a second position to compress the diaphragm to express the agent from the chamber, and that is returned from the second position to the first position when the diaphragm is moved to the decompressed position as the chamber is filled with the agent.

7. A device for the administration of a liquid therapeutic agent to a patient, comprising:
   a housing defining a fluid flow conduit having an upstream portion and a downstream portion;
   a chamber in the housing having an inlet lumen in fluid communication with the upstream portion, and first and second outlet lumens separately in communication with the downstream portion;
   a check valve in fluid communication with the second outlet lumen that is responsive to a predetermined cracking pressure to allow fluid flow from the second outlet lumen to the downstream portion; and
   a bolus dose delivery mechanism that is selectively actuable to (a) apply a pressure to the chamber that is at least equal to the cracking pressure to express a predetermined volume of the agent from the chamber through the second outlet lumen and the check valve, and (b) allow a refilling of the chamber with the agent through the first inlet lumen while also allowing a continuous flow of the agent from the chamber through the first outlet lumen.

8. The device of claim 7, wherein the bolus dose delivery mechanism comprises:
   a resilient diaphragm disposed as a sealing closure for the chamber and movable between a compressed position when the chamber is voided of the agent and a decompressed position when the chamber is filled with the agent.

9. The device of claim 8, further comprising a plunger that is engageable against the diaphragm and that is manually movable from a first position to a second position to compress the diaphragm to express the agent from the chamber, and that is returned from the second position to the first position when the diaphragm is moved to the decompressed position as the chamber is filled with the agent.

10. The device of claim 8, wherein the agent flows from the inlet lumen through the chamber and through the first outlet lumen when the diaphragm is in the decompressed position, and the agent flows from the chamber through the second outlet lumen and the check valve only in response to the creation of the cracking pressure in the second outlet lumen.

11. The device of claims 7, 8, 9, or 10, further comprising:
    a first flow-restricting orifice in the upstream portion; and
    a second flow-restricting orifice in the first outlet lumen.

12. The device of claims 7, 8, 9, or 10, wherein the check valve comprises:
    a tubular element having an upstream end in fluid communication with the second outlet lumen and a downstream end in fluid communication with the downstream portion through a valve orifice; and
    a flexible membrane secured to the tubular element so as to close the valve orifice when the pressure in the second outlet lumen is less than the cracking pressure, whereby the membrane opens the valve orifice in response to the pressure in the second outlet lumen being at least equal to the cracking pressure.

13. The device of claim 11, wherein the check valve comprises:
    a tubular element having an upstream end in fluid communication with the second outlet lumen and a downstream end in fluid communication with the downstream portion through a valve orifice; and
    a flexible membrane secured to the tubular element so as to close the valve orifice when the pressure in the second outlet lumen is less than the cracking pressure, whereby the membrane opens the valve orifice in response to the pressure in the second outlet.

14. A system for the delivery of a liquid therapeutic agent to a patient, comprising:
    a pressurized source for the agent; and
    a patient-controllable delivery device having an upstream conduit portion in fluid communication with the source and a downstream conduit portion in fluid communication with a delivery conduit, the device comprising:
    a chamber having an inlet lumen in fluid communication with the upstream portion, and first and second outlet lumens separately in communication with the downstream portion;
    a check valve in fluid communication with the second outlet lumen that is responsive to a predetermined cracking pressure to allow fluid flow from the second outlet lumen to the downstream portion; and
    a bolus dose delivery mechanism that is selectively actuable to (a) apply a pressure to the chamber that is at least equal to the cracking pressure to express a predetermined volume of the agent from the chamber through the second outlet lumen and the check valve, and (b) allow a refilling of the chamber with the agent through the first inlet lumen while also allowing a continuous flow of the agent from the chamber through the first outlet lumen.

15. The system of claim 14, wherein the bolus dose delivery mechanism comprises:

a resilient diaphragm disposed as a sealing closure for the chamber and movable between a compressed position when the chamber is voided of the agent and a decompressed position when the chamber is filled with the agent.

16. The system of claim 15, wherein the agent flows from the inlet lumen through the chamber and through the first outlet lumen when the diaphragm is in the decompressed state, and the agent flows from the chamber through the second outlet lumen and the check valve only in response to the creation of the cracking pressure in the second outlet lumen.

17. The device of claim 14, further comprising a plunger that is engageable against the diaphragm and that is manually movable from a first position to a second position to compress the diaphragm to express the agent from the chamber, and that is returned from the second position to the first position when the diaphragm is moved to the decompressed position as the chamber is filled with the agent.

18. The system of claims 14, 15, or 16, further comprising:

a first flow-restricting orifice in the upstream portion; and a second flow-restricting orifice in the first outlet lumen.

19. The device of claim 17, wherein the check valve comprises:

a tubular element having an upstream end in fluid communication with the second outlet lumen and a downstream end in fluid communication with the downstream portion through a valve orifice; and a flexible membrane secured to the tubular element so as to close the valve orifice when the pressure in the second outlet lumen is less than the cracking pressure, whereby the membrane opens the valve orifice in response to the pressure in the second outlet lumen being at least equal to the cracking pressure.

20. The system of claims 14, 15, or 16, wherein the check valve comprises:

a tubular element having an upstream end in fluid communication with the second outlet lumen and a downstream end in fluid communication with the downstream portion through a valve orifice; and a flexible membrane secured to the tubular element so as to close the valve orifice when the pressure in the second outlet lumen is less than the cracking pressure, whereby the membrane opens the valve orifice in response to the pressure in the second outlet lumen being at least equal to the cracking pressure.

* * * * *